United States Patent [19]

Kiyomine et al.

[11] Patent Number: 5,720,945
[45] Date of Patent: Feb. 24, 1998

[54] 1,3-BUTANEDIOL THIOGLYCOLLATE ISOMER MIXTURE AND PERMANENT WAVING COMPOSITION COMPRISING SAME

[75] Inventors: Akira Kiyomine, Kawachi-gun; Yukihiro Kondo, Utsunomiya, both of Japan; Kenichi Morita, Bensheim, Germany; Shinobu Nagase, Haga-gun, Japan; Koichi Nakamura; Yoshinori Nishizawa, both of Utsunomiya, Japan; Bernd Nöcker, Ober-Ramstadt, Germany; Hitoshi Sakaguchi, Haga-gun; Hiroyuki Suzuki, Kawachi-gun, both of Japan

[73] Assignee: Kao Corporation, Japan

[21] Appl. No.: 620,024

[22] Filed: Mar. 21, 1996

[30] Foreign Application Priority Data

Mar. 30, 1995 [JP] Japan ................ 7-072967
May 17, 1995 [DE] Germany ........... 195 18 115.8

[51] Int. Cl.⁶ .................... A61K 7/09; A61K 7/07
[52] U.S. Cl. .......................... 424/70.5; 424/70.2
[58] Field of Search ..................... 424/70.5, 70.2

[56] References Cited

U.S. PATENT DOCUMENTS

| 5,068,102 | 11/1991 | Tennigkeit | 424/70.5 |
| 5,332,570 | 7/1994 | Bergstrom | 424/72 |
| 5,378,454 | 1/1995 | Burmeister | 424/70.5 |
| 5,612,023 | 3/1997 | Kiyomine | 424/70.5 |

OTHER PUBLICATIONS

Zviak, *The Science of Hair Care*, 1986 pp. 190–193, (1986).

*Primary Examiner*—Sally Gardner-Lane

[57] ABSTRACT

The object of the invention is a new isomer mixture of 3-hydroxybutyl monothioglycollate and 3-hydroxy-1-methyl propyl monothioglycollate in a weight proportion of about 1.5:1 to 4:1, preferably about 2:1 to about 3:1, comprising less than 5%, preferably less than 2% by wt., of 1,3-butanediol thioglycollate, and its use as the sole or main reducing agent in compositions for permanent waving of human hair. The compositions have reduced smell, good waving properties and an extremely low sensitizing potential on human skin.

6 Claims, No Drawings

1,3-BUTANEDIOL THIOGLYCOLLATE ISOMER MIXTURE AND PERMANENT WAVING COMPOSITION COMPRISING SAME

This invention refers to 1,3-butanediol thioglycollate comprising essentially an isomer mixture of 3-hydroxybutyl monothioglycollate and 3-hydroxy-1-methyl propyl monothioglycollate and a composition for the permanent waving of human hair comprising this isomer mixture.

It is well-known that permanent waving is usually performed in two steps:
The reductive splitting of the cystine disulfide bonds of the hair by the action of a reducing agent, and the subsequent neutralizing or fixing process by the application of an oxidizing agent, whereby the cystine disulfide bonds are re-established.

The reducing agent mainly used is still thioglycolic acid, particularly its ammonium salt, although numerous other thio compounds have been suggested for this purpose, e.g. thiolactic acid, 3-mercaptopropionic acid, thiotartaric acid, thiomalic acid, dimercaptoadipinic acid, cysteine, N-acetyl cysteine, homocysteine and other mercaptocarboxylates, cysteamine, N-acyl cysteamine and other cysteamine derivatives, 2-mercaptoethanol, thioglycerol, 3-alkoxy-1-mercapto-propanols and other mercapto-alcohols, methyl thioglycollate, ethyl thioglycollate, glycol monothioglycollates, 1,2-propyleneglycol monothioglycollate, 1,3-propyleneglycol monothioglycollate, glycerol monothioglycollate, glycol monothiolactate, glycerol monothiolactate, glycerol mono-3-mercaptopropionate, cysteine methyl ester, cysteine ethyl ester, homocysteine methyl ester, homocysteine ethyl ester and other mercaptocarboxylates, thioglycolic amide, N-hydroxyethyl thioglycolic amide, 3-mercaptopropionic amide, N-hydroxyethyl 3-mercaptopropionic amide, cysteine amide and other mercaptocarboxylic acid amides which, however, have not been successful in practice.

The thioglycollate compositions are usually applied at a pH-value between 8 and 10, particularly 8.5 to 9.5, which may lead to hair damage if applied repeatedly within short intervals.

It has already been tried to overcome these disadvantages by the creation of so-called "acidic permanent waving compositions" having a pH at use of about 6.8 to 7.8, i.e. close to neutral. The reducing agent mainly used in these compositions is thioglycolic acid monoglycerol ester. However, this substance is supposed to have an irritating and especially sensitizing effect on some users so that this solution of the problem is not optimal.

It has now been found that these problems may be overcome while obtaining permanent waving compositions acting at a pH-value where no hair damage occurs but which still have a good waving effect, if a composition is used comprising as reducing agent 1,3-butanediol monothioglycollate in a certain isomer combination alone or in admixture with other reducing agents.

German Patent Application No. 40 03 234 already discloses permanent waving compositions comprising as active agents, i.e. reducing agents, monothiolactic acid glycerol ester. It also contains a survey of the state of the art, to which reference is expressly made.

Moreover, German Patent No.39 20 984 describes permanent waving compositions comprising mixtures of glycerol monothioglycollate and 2- or 3-mercaptopropionic acid monoglycerol ester.

All these compositions and mixtures, however, are not optimal in respect of their waving effect, and may cause skin sensitization of the persons treated thereby and, particularly, of the hairdresser too if applied repeatedly.

German Patent Application No.22 55 800 already describes permanent waving compositions containing as active agents, i.e. reducing agents, esters from polyvalent alcohols and low mercapto carboxylic acids. As such, 1,2-propyleneglycol monothioglycolic acid ester is mentioned.

This course is continued by Patent Application WO-A 93/0179, describing an azeotropic mixture of two isomers of 1,2-propanediol monothioglycollate and its use as reducing agent in permanent waving compositions.

According to the invention, it has been found that a permanent waving composition comprising a preferably azeotropic mixture of 3-hydroxybutyl monothioglycollate of the following formula (I) and 3-hydroxy-1-methyl propyl thioglycollate of the following formula (II) in a weight proportion of about 1.5:1 to about 4:1, particularly 2:1 to 3:1, has at least the same permanent waving properties as thioglycolic acid ester with polyvalent alcohols, such as ethyleneglycol monothioglycollate, 1,2-propyleneglycol monothioglycollate, 1,3-propyleneglycol monothioglycollate and glycerol monothioglycollate, but does not cause any sensitization, has a less intensive odor than the above cited esters and, therefore, has superior properties compared with these thioglycolic acid esters. From this isomer mixture homogeneous permanent waving compositions on an aqueous basis may be produced.

Thus, the present invention relates to an isomer mixture of 1,3-butanediol thioglycollates comprising a preferably azeotropic mixture of 3-hydroxybutyl monothioglycollate, represented by the following formula (I)

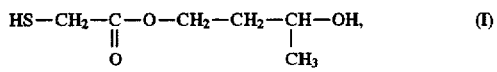

and 3-hydroxy-1-methoxypropyl monothioglycollate, represented by the following formula (II)

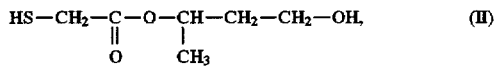

in a weight proportion of about 1.5:1 to about 4:1.

There are no problems in respect of the water-solubility of the isomer mixture of 3-hydroxybutyl monothioglycollate and 3-hydroxy-1-methyl propyl monothioglycollate according to the invention, provided that the percentage of the by-product 1,3-butanediol dithioglycollate does not exceed 5% by wt., particularly 2.5% by wt., preferably 1% by wt., of the total ester mixture.

According to the invention, the isomer mixture, i.e. 1,3-butanediol thioglycollate, is produced by the following reaction:

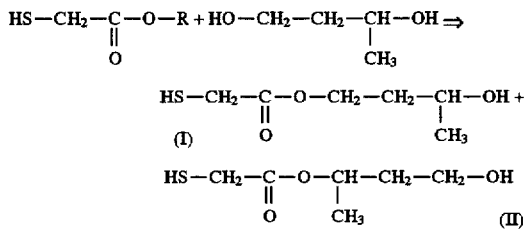

(In these formulae R denotes a hydrogen atom or a low alkyl group bearing 1 to 4 carbon atoms).

Thus, thioglycolic acid or alkyl thioglycollates react with 1,3-butanediol (4) to yield an isomer mixture of 3-hydroxybutyl monothioglycollate (I) and 3-hydroxy-1-methyl propyl monothioglycollate (II).

This reaction may be performed without or with a solvent such as toluene or 1,2-dichloroethane. The reaction may be effected without or with a catalyst such as sulfuric acid, benzene sulfonic acid or p-toluene sulfonic acid. The preferred reaction temperature is about 50° C. to 200° C., and, particularly preferred, about 80° C. to 180° C. The molar ratio of 1,3-butanediol to thioglycolic acid or alkyl thioglycollate lies preferably between 1 and 20, particularly between 1.5 and 3. To improve the reaction, the water that develops during the reaction is preferably removed. After completion of the reaction, the components (I) and (II) of the prepared mixture are easily purified by means of column chromatography. To improve compatibility, the quantity of the diester co-produced so far should not exceed 2% by wt.

In addition to the isomer mixture according to the invention, the permanent waving composition may comprise further known reducing agents, e.g., one or more compounds selected from the group of thioglycolic acid, thiolactic acid, thiomalic acid, thiotartaric acid, dimercaptoadipinic acid, cysteine, N-acetyl cysteine, cysteine amide, homocysteine, cysteamine, N-acetyl cysteamine, mercaptoethanol, thioglycerol, ethyleneglycol monothioglycollate, 1,2-propyleneglycol monothioglycolate, 1,3-propyleneglycol monothioglycollate, glycol monothiolactrate, glycerol monothiolactate and the salts thereof, provided that they do not have a negative influence on the effect of the reducing agent according to the invention.

The total proportion of 1,3-butanediol dithioglycollate shall not exceed 5% by wt., calculated to the mixture of monothioglycollate, it shall preferably be less than 2.5% by wt., particularly only 1% by wt. or less.

The preferred proportion of 1,3-butanediol monothioglycollate in the permanent waving compositions according to the invention is about 5% to 30% by wt., calculated to the total reducing composition (i.e., excluding the fixing or neutralizing agent), particularly between about 10% to 15% and about 25% by wt.

If other reducing agents are present in admixture with 1,3-butanediol thioglycollate in the permanent waving compositions according to the invention, their proportion is preferably below 50%, particularly below 25%, calculated to the total percentage of reducing agents.

In any case, however, the isomer mixture represents the main proportion of the total reducing agent, preferably between 65% and 100% therefor.

If 1,3-butanediol thioglycollate is used in admixture with other reducing agents, its proportion of the total reducing agent content must naturally be reduced accordingly; the quantity depends on the type and proportion of the other reducing agents.

The total reducing agent content is normally 2.5% to about 15% by wt., calculated to free thioglycolic acid as reference substance.

If required, the reducing permanent waving compositions may contain a quantity of alkalizing agents. Their amount depends on the character of the reducing ingredient and the desired pH-value of the composition. The reducing agent composition preferably comprises about 0.1% to about 5%, particularly between about 0.5% and about 2.5% by wt. thereof.

Within the scope of the invention, preferred alkalizing agents are ammonium carbamate, ammonia, and (or) ammonium (bi)carbonate. The preferred pH-value is in the range between about 6.5 and about 9.5, preferably about 7 to 8.5.

The permanent waving compositions according to the invention preferably also contain surfactants. Their proportion is about 0.1% to about 10%, particularly about 1% to about 5% by wt. of the reducing agent composition.

The surfactants used for both reducing agent compositions and neutralizing compositions are preferably the known anionic compounds which may optionally also be used in combination with nonionic surfactants.

Suitable anionic surfactants are particularly the known alkyl ether sulfates and carboxylic acids, preferably in the form of their alkali salts, and protein fatty acid condensates.

Suitable nonionic surfactants are particularly $C_8-C_{18}$-fatty alcohol polyglycol ethers, fatty acid polyglycol esters, fatty acid alkanolamides, amine oxides and, mostly preferred, $C_8-C_{18}$-alkyl polyglucosides.

Amphoteric surfactants may also be used, such as the known betaines and amido betaines and, particularly in cationic neutralizing agents, cation-active surfactants such as quaternary ammonium compounds.

Other desirable components of the reducing agent compositions according to the invention are $C_3-C_6$-alkanediols or the ethers thereof, particularly mono-$C_1-C_3$-alkyl ethers.

Preferred substances in this context are 1,2- and 1,3-propanediol, 1-methoxypropanol(-2), 1-ethoxypropanol(-2), 1,3- and 1,4-butanediol, diethyleneglycol, and the monomethyl and monoethyl ethers thereof as well as dipropyleneglycol and the monomethyl and monoethyl ethers thereof.

The percentage of these diols is preferably between 0.5% and 30%, more preferably from about 1% to about 15%, particularly about 5% to about 10% by wt. of the reducing agent composition.

In addition to $C_3-C_6$-alkanediols or the ethers thereof, mono-alcohols may also be used, such as ethanol, propanol-1, propanol-2, as well as polyalcohols such as glycerol and hexanetriol, ethyl carbitol, benzyl alcohol, benzyl oxyethanol, and propylene carbonate (4-methyl 1,3-dioxolane-2-on), N-alkyl pyrrolidone and urea.

The compositions according to the invention may naturally comprise any ingredients common in permanent waving compositions; they may be present as (aqueous) solutions, emulsions, creams, foams, etc.

To avoid repetition, reference is made to the state of the art, as described, e.g., in "Ullmann's Encyclopedia of Chemical Chemistry", Vol. A12 (1986), pp. 588 to 591, and particularly the monography of K. Schrader, "Grundlagen und Rezepturen der Kosmetika", 2nd Ed. (1989, H üthig-Verlag, Heidelberg), pp. 823 to 840, as well as the survey of D. Hollenberg et al. in "Seifen-Öle-Fette-Wachse" 117 (1991), pp.81 to 87.

The compositions and ingredients disclosed therein are expressly included and may also be used within the scope of the present invention.

Optionally a pre-treatment may be applied before the application of the reducing agent as described, e.g., in German Patent Application No.37 40 926. After that, the hair is wound on curlers, then the reducing agent is applied. After about 15 to 30 minutes processing time and rinsing with water, the hair is neutralized with one of the usual peroxide or bromate compositions which are well-known from the state of the art.

Of course, an intermediate treatment known per se may also be applied between the reducing and the neutralizing steps.

The following Examples illustrate the invention in detail.

PRODUCTION EXAMPLE 1

Synthesis of an isomer mixture of 3-hydroxybutyl monothioglycollate and 3-hydroxy-1-methyl propyl monothioglycollate (1,3-butanediol monothioglycollate)

In a reaction vessel a mixture of 73.4 g (0.841 moles) 1,3-butanediol and 50.0 g (0.534 moles) thioglycolic acid are stirred at 170° C. to 180° C. under nitrogen atmosphere for three hours. After completion of the reaction, the liquid is cooled down and a mixture is obtained consisting of 50% of an isomer mixture of 3-hydroxybutyl monothioglycollate and 3-hydroxy-1-methyl propyl monothioglycollate as well as of 20% 1,3-butanediol dithioglycollate and of 30% 1,3-butanediol. The yield of 1,3-butanediol monothioglycollates was 63%. The weight ratio of 3-hydroxybutyl monothioglycollate and 3-hydroxy-1-methyl propyl monothioglycollate was determined by liquid chromatography as being about 2:1.

The reaction product was purified as follows:

The mixture obtained was distilled under vacuum (0.1 to 0.2 mmHg); after removal of 47.4 g of the initial product at 81° C. to 85° C., 39.7 g of the isomer mixture were obtained in a quantity of >99%. The isomer mixture of 3-hydroxybutyl monothioglycollate and 3-hydroxy-1-methyl propyl monothioglycollate contained <1% of 1,3-butanediol dithioglycollate. The total yield was 45%.

The results of the $^1$H-NMR spectrum and liquid chromatography analysis confirmed that the weight proportion of 3-hydroxybutyl monothioglycollate to 3-hydroxy-1-methyl propyl monothioglycollate in the azeotropic mixture was about 2:1.

PRODUCTION EXAMPLE 2

In a reaction vessel 127.3 g (1.41 moles) 1,3-butanediol, 50.0 g (0.471 moles) methyl thioglycollate, and 0.5 g sulfuric acid are stirred under nitrogen atmosphere at 100° C. for two hours. After completion of the reaction, the mixture was purified twice by silica column chromatography (1.2 kg Si 60 [Merck], mesh 230 to 400, elution solvent: chloroform and chloroform/methanol in a proportion of 49:1). The solvent was evaporated from the eluate; after drying, 26.7 g (0.163 moles) of an isomer mixture of 3-hydroxybutyl monothioglycollate and 3-hydroxy-1-methyl propyl monothioglycollate were obtained, corresponding to a 35% yield. The purity was >99%.

The $^1$H-NMR-spectrum analysis confirmed that the weight proportion of 3-hydroxybutyl monothioglycollate to 3-hydroxy-1-methyl propyl monothioglycollate was about 3:1. $^1$H-NMR-spectrum (DMSO-d$_6$) δ/ppm: Peak readings for 3-hydroxybutyl monothioglycollate: 1.08 (3H, d, H$^F$), 1.57–1.75 (2H m, H$^D$) 2.92 (1H br, H$^A$), 3.29 (2H, d, H$^B$), 3.71 (1H, m, H$^E$), 4.12 (2H, 2H, t, H$^C$), 4.56 (1H, d, H$^G$).

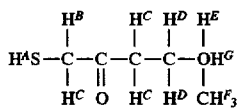

Peak readings for 3-hydroxy-1-methyl propyl monothioglycollate: 1.19 (3H, d, H$^f$), 1.57–1.75 (2 H, m, H$^d$) 2.92 (1H br, H$^a$), 3.35 (2H, d, H$^b$), 3.44 (2H, td, H$^c$), 4.49 (1H, t, H$^g$), 4.93 (1H, m, H$^e$).

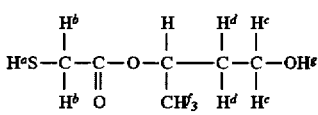

EXAMPLES 1 TO 3

Three permanent waving compositions were prepared comprising the same molar SH quantities for each reducing agent composition.

Stability Tests

TABLE 1

| Reducing agent mixture: | |
|---|---|
| N1: | Mixture comprising 50% of an isomer mixture of 3-hydroxybutyl monothioglycollate and 3-hydroxy-1-methyl propyl monothioglycollate in a weight proprotion of 2:1, 20% 1,3-butanediol dithioglycollate, and 30% 1,3-butanediol. |
| N2: | Isomer mixture of 3-hydroxybutyl monothioglycollate and 3-hydroxy-1-methyl propyl monothioglycollate in a weight proportion of 2:1 (min. contents 99%). |
| N3: | Isomer mixture of 3-hydroxybutyl monothioglycollate and 3-hydroxy-1-methyl propyl monothioglycollate in a weight proportion of 3:1 (min. contents 99%). |

TABLE 2

|  | Example 1 | Example 2 | Example 3 |
|---|---|---|---|
| N1 | 12.0 g | — | — |
| N2 | — | 9.3 g | — |
| N3 | — | — | 9.3 g |
| NH$_4$HCO$_3$ | 0.87 g | 0.87 g | 0.87 g |
| 28% NH$_4$OH | q.s. | q.s. | q.s. |
| Water | @ 100 g | @ 100 g | @ 100 g |
| pH-value | 7.2 | 7.2 | 7.2 |

The stability tests of compositions 1 to 3 showed the following results:

Composition according to Example 1 (comprising reducing agent N1):

Becoming turbid immediately after mixing and separating into two layers 10 minutes later.

Composition according to Example 2 (comprising recucing agent N2):

The composition was a homogeneous, transparent, and permanently stable solution.

Composition according to Example 3 (comprising reducing agent N3):

The composition was a homogeneous, transparent, and permanently stable solution.

Odor Tests

The odor of the compositions according to the following Table 3 (each comprising equal molar quantities of reducing ingredients) was evaluated in a blind test.

TABLE 3

|  | Example 4 | Comparison Example I |
|---|---|---|
| N2 | 9.3 g | — |
| N4 | — | 8.5 g |
| NH$_4$HCO$_3$ | 0.87 g | 0.87 g |
| 28% NH$_4$OH | q.s. | q.s. |
| Water | @ 100 g | @ 100 g |
| pH-value | 7.2 | 7.2 |

N4 represented a mixture comprising 1,2-propyleneglycol monothioglycollates according to the state of the art.

Results of the odor test:

Composition according to Example 4 (comprising reducing agent N2):

Only a weak characteristic smell was noted.

Composition according to Comparison Example I (comprising reducing agent N4):

A strong characteristic smell was noted.

EXAMPLES 5 AND 6 AND COMPARISON EXAMPLE II

In each case the compositions of Table 4 comprise the same molar SH quantities of reducing agents. Damaged hair (European hair) was subjected to permanent waving treatments using in each case the same compositions (i.e., permanent waving at room temperature for 10 minutes each; rinsing with water, thereafter treatment with the neutralizing composition at room temperature for 10 minutes); then evaluation of the waving effect.

TABLE 4

| Examples | 5 | 6 | Comparison Example II. |
|---|---|---|---|
| N1 | — | — | — |
| N2 | 9.3 g | — | — |
| N3 | — | 9.3 g | — |
| N5 | — | — | 5.2 g |
| $NH_4HCO_3$ | 0.87 g | 0.87 g | 0.87 g |
| 28% $NH_4OH$ | q.s. | q.s. | q.s. |
| Water | @ 100 g | @ 100 g | @ 100 g |
| pH-value | 7.2 | 7.2 | 7.2 |

The reducing agents N2 and N3 are the same as listed in Table 1.
N5 represents ammonium thioglycollate.

| Neutralizing Composition | |
|---|---|
| 35% Hydrogen peroxide | 7.1 g |
| Phosphoric acid | q.s. |
| Water | @ 100 g |
| pH-value | 3.5 |

Evaluation of waving performance:
Composition according to Example 5 (reducing agent N2):
 The hair showed a completely uniform permanent waving.
Composition according to Example 6 (reducing agent N3):
 The hair showed a completely uniform permanent waving.
Composition according to Comparison Example II (reducing agent N5):
 A considerably non-uniform permanent waving result was noted.

EXAMPLE 7

Damaged European human hair was treated as described in Example with the permanent waving solution described in the following formula and fixed with a corresponding neutralizer.

| N2 | 7.0 g |
|---|---|
| N5 | 1.3 g |
| $NH_4HCO_3$ | 0.87 g |
| 28% $NH_4OH$ | q.s. |
| Water | @ 100 g |
| pH-value | 7.2 |

Evaluation of the permanent waving results:
 The hair showed a completely uniform permanent waving, no excessive perming was noted.

Sensitivity Test

The sensitizing potential of isomer mixture N2 was tested vs. glycerol monothioglycollate (GMTG) in the well-known Guinea Pig Maximization Test according to Magnusson and Kligman.

Results

Reducing agent N2:
 In a group of 10 sensitized animals no positive reaction occurred.
Glycerol monothioglycollate:
 In a group of 10 sensitized animals a positive reaction was noted in 7 cases.

These tests prove that effective permanent waving compositions without sensitizing effect are obtained by using the isomer mixture according to the invention as reducing compound.

The following Examples describe two optimally composed permanent waving preparations comprising the isomer mixture according to the invention. Neutralization is performed with a usual neutralizing agent on the basis of hydrogen peroxide.

EXAMPLE 8

| Permanent wave for normal hair | |
|---|---|
| Isomer mixture of 3-hydroxybutyl monothioglycollate and 3-hydroxy-1-methyl propyl monothioglycollate (weight ratio about 2.5:1; content of 1,3-butanediol dithioglycollate <1.5% by wt.) | 19.0 (% by wt.) |
| Chlorophyllin | 0.005 |
| Ammonium hydrogencarbonate | 0.9 |
| Quaternary cationic polymer (Polyquaternium-2) | 0.5 |
| 1,3-Butanediol | 5.0 |
| Octyl phenol ethoxylate | 4.0 |
| Castor oil polyglycol fatty acid ester | 0.5 |
| Perfume | 0.4 |
| Water | @ 100.0 |
| Adjusted with ammonia to pH | 7.0 |

EXAMPLE 9

| Permanent wave for porous hair | |
|---|---|
| Isomer mixture of 3-hydroxybutyl monothioglycollate and 3-hydroxy-1-methyl propyl monothioglycollate (weight ratio about 2:1; content of 1,3-butanediol dithioglycollate about 1% by wt.) | 13.75 (% by wt.) |
| Ammonium carbamate | 0.40 |
| Protein hydrolyzate (Nutrilan ®) | 0.30 |
| Coconut amidopropyl betaine | 2.00 |
| Lauryl alcohol ethoxylate (Laureth-23) | 1.00 |
| Perfume oil | 0.40 |
| Water | @ 100.00 |
| Adjusted with ammonia to pH | 7.1. |

We claim:
1. A 1,3-Butanediol thioglycollate composition consisting essentially of an isomer mixture of 3-hydroxybutyl monothioglycollate of the formula

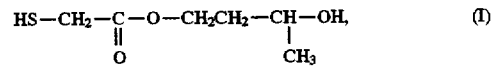

and 3-hydroxy-1-methyl propyl monothioglycollate of the formula

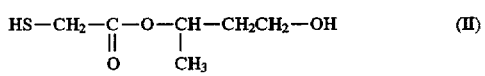

wherein an azeotropic isomer mixture of said 3-hydroxybutyl monothioglycollate (I) and said 3-hydroxy-1-methyl propyl monothioglycollate (II) is present in a weight proportion of about 1.5:1 to about 4:1, and wherein the proportion of 1,3-butanediol dithioglycollate is less than 5% by wt., calculated to the isomer mixture.

2. Isomer mixture according to claim 1, wherein the weight proportion of (I) to (II) is about 2:1 to about 3:1.

3. Isomer mixture according to claim 1, wherein the proportion of 1,3-butanediol dithioglycollate is less than 2% by wt., calculated to the total isomer mixture.

4. A composition for permanent waving of human hair comprising an isomer mixture of 3-hydroxybutyl monothioglycollate of the formula

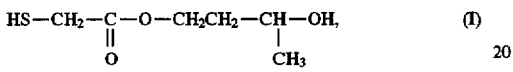

and 3-hydroxy-1-methyl propyl monothioglycollate of the formula

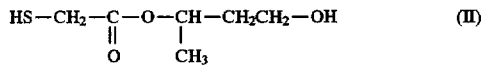

wherein an azeotropic isomer mixture of said 3-hydroxybutyl monothioglycollate (I) and said 3-hydroxy-1-methyl propyl monothioglycollate (II) is present in a weight proportion of about 1.5:1 to about 4:1, and wherein the proportion of 1,3-butanediol dithioglycollate is less than 5% by wt., calculated to the isomer mixture.

5. Composition according to claim 4, further comprising one or more additional reducing agents, selected from the group consisting of thioglycolic acid, thiolactic acid, thiomalic acid, thiotartaric acid, dimercaptoadipinic acid, cysteine, N-acetyle cysteine, cysteine amide, homocysteine, cysteamine, N-acetyle cysteamine, mercaptoethanol, thioglycerol, ethanediol monothioglycollate, glycerol monothioglycollate, 1,2-propanediol monothioglycollate, 1,3-propanediol monothioglycollate, ethanediol monothiolactate, 1,2-propanediol monothiolactate, and 1,3-propanediol monothiolactate.

6. Composition according to claim 4 further comprising one or more compounds selected from the group of ethanol, propanol-1, propanol-2, 1,2-propanediol, 1,3-butanediol, hexanetroil, glycerol, ethyl carbitol, benzyl alcohol, benzyl oxyethanol, urea and 2-methyl pyrrolidone.

* * * * *